US012643890B2

(12) United States Patent
Brom et al.

(10) Patent No.: US 12,643,890 B2
(45) Date of Patent: Jun. 2, 2026

(54) SUBSTITUTED AMINO-PYRIMIDINES

(71) Applicant: Hoffmann-La Roche Inc., Little Falls, NJ (US)

(72) Inventors: Virginie Brom, Blotzheim (FR); Luke Green, Basel (CH); Christian Kramer, Lörrach (DE); Dmitry Mazunin, Grenzach-Wyhlen (DE); Emmanuel Pinard, Linsdorf (FR); Hasane Ratni, Habsheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 495 days.

(21) Appl. No.: 18/062,896

(22) Filed: Dec. 7, 2022

(65) Prior Publication Data

US 2023/0112172 A1 Apr. 13, 2023

Related U.S. Application Data

(63) Continuation of application No. PCT/EP2021/065084, filed on Jun. 7, 2021.

(30) Foreign Application Priority Data

Jun. 8, 2020 (EP) .................................... 20178658

(51) Int. Cl.

| | |
|---|---|
| ***C07D 403/04*** | (2006.01) |
| ***A61K 31/506*** | (2006.01) |
| ***A61P 1/16*** | (2006.01) |
| ***A61P 13/12*** | (2006.01) |
| ***A61P 17/00*** | (2006.01) |
| ***A61P 25/00*** | (2006.01) |
| ***A61P 29/00*** | (2006.01) |
| ***C07D 413/04*** | (2006.01) |

(52) U.S. Cl.

CPC ......... *C07D 413/04* (2013.01); *C07D 403/04* (2013.01)

(58) Field of Classification Search

CPC .. C07D 403/04; C07D 413/04; A61K 31/506; A61P 1/16; A61P 13/12; A61P 17/00; A61P 25/00; A61P 29/00

See application file for complete search history.

(56) References Cited

U.S. PATENT DOCUMENTS

| | | | |
|---|---|---|---|
| 2021/0363152 | A1 | 11/2021 | Baccei et al. |
| 2023/0123268 | A1 | 4/2023 | Beurier et al. |
| 2023/0174516 | A1 | 6/2023 | Beurier et al. |

FOREIGN PATENT DOCUMENTS

| | | | |
|---|---|---|---|
| JP | 2019-518799 | A | 7/2019 |
| WO | 2018/212534 | A1 | 11/2018 |
| WO | 2021/043260 | A1 | 3/2021 |

OTHER PUBLICATIONS

"International Preliminary Report on Patentability—PCT/EP2021/065084" (Report Issuance Date: Dec. 13, 2022; Chpater I),:pp. 1-7 (Dec. 22, 2022).

"International Search Report—PCT/EP2021/065084" (w/Written Opinion),:pp. 1-11 (Jul. 29, 2021).

USPTO, U.S. Appl. No. 18/062,644, filed Dec. 7, 2022.

Cancer [online], [retrieved on Jul. 6, 2007] Retrieved from the Internet, URL: http://www.nlm.nih.gov/medlineplus /cancer.html, pp. 1-10 (Jul. 6, 2007).

Golub et al., "Molecular Classification of Cancer: Class Discovery and Class Prediction by Gene Expression Monitoring," Science 286:531-537 (Oct. 15, 1999).

"International Preliminary Report on Patentability—PCT/EP2021/065111" (Report Issuance Date: Dec. 13, 2022; Chapter I), pp. 1-7 (Dec. 22, 2022).

"International Preliminary Report on Patentability—PCT/EP2021/065106" (Report Issuance Date: Dec. 13, 2022; Chapter I), pp. 1-7 (Dec. 22, 2022).

"International Search Report—PCT/EP2021/065111" (w/Written Opinion), pp. 1-11 (Sep. 17, 2021).

"International Search Report—PCT/EP2021/065106" (w/Written Opinion), pp. 1-11 (Sep. 17, 2021).

Lala et al., "Role of Nitric Oxide in Tumor Progression: Lessons from Experimental Tumors," Cancer and Metastasis Reviews, 17:91-106 (1998).

*Primary Examiner* — Brenda L Coleman

(74) *Attorney, Agent, or Firm* — Sarah E. Tully

(57) ABSTRACT

The invention provides novel compounds having the general formula I

I

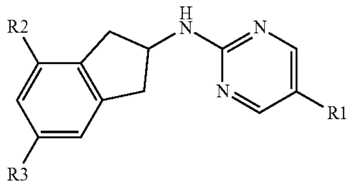

wherein $R^1$, $R^2$, and $R^3$ are as defined herein, compositions including the compounds and methods of using the compounds.

11 Claims, No Drawings

SUBSTITUTED AMINO-PYRIMIDINES

CROSS-REFERENCE TO RELATED APPLICATIONS

This application is a continuation of International Patent Application No. PCT/EP2021/065084 filed on Jun. 7, 2021, which is entitled to the benefit of European Application No. EP20178658.9 filed on Jun. 8, 2020, the disclosures of which are incorporated herein by reference.

FIELD OF THE INVENTION

This invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

BACKGROUND OF THE INVENTION

Autotaxin (ATX) is a secreted enzyme also called ectonucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors.

The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

SUMMARY OF THE INVENTION

The present invention provides novel compounds of formula I

I

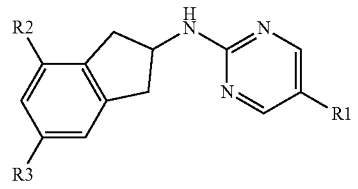

wherein $R^1$ is selected from the group consisting of:
- i) 5 or 6 member heteroaryl
- ii) 5 or 6 member substituted heteroaryl
- iii) 5 or 6 member heterocycloalkyl
- iv) 5 or 6 member substituted heterocycloalkyl wherein substituted heteroaryl or substituted heterocycloalkyl is substituted with one or more alkyl substituents;

$R^2$ is selected from the group consisting of
- i) H,
- ii) cyano,
- iii) halogen,
- iv) $C_{1-6}$-alkyl
- v) halo-$C_{1-6}$-alkyl $R^3$ is selected from the groups consisting of
- i) H,
- ii) halogen,
- iii) $C_{1-6}$-alkyl
- iv) halo-$C_{1-6}$-alkyl or pharmaceutically acceptable salts.

Furthermore, the invention includes all racemic mixtures, all their corresponding enantiomers and/or optical isomers.

In accordance with the invention, the compounds of formula I or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula I or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula I and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and—chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particulary, the compounds of formula I and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

DETAILED DESCRIPTION OF THE INVENTION

The term "$C_{1-6}$-alkyl" denotes a monovalent linear or branched saturated hydrocarbon group of 1 to 6 carbon atoms. In some embodiments, if not otherwise described, alkyl comprises 1 to 6 carbon atoms ($C_{1-6}$-alkyl), or 1 to 4 carbon atoms ($C_{1-4}$-alkyl). Examples of $C_{1-6}$-alkyl include methyl, ethyl, propyl, isopropyl, n-butyl, iso-butyl, sec-butyl, tert-butyl and pentyl. Particular alkyl groups include methyl, isopropyl and tert-butyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

The term "cyano" denotes a —C≡N group.

The term "halogen", "halide" and "halo" are used interchangeably herein and denote fluoro, chloro, bromo or iodo. Particular halogen is chloro.

The term "halo-$C_{1-6}$-alkyl" denotes a $C_{1-6}$-alkyl group wherein at least one of the hydrogen atoms of the $C_{1-6}$-alkyl group has been replaced by the same or different halogen atoms. Particular examples are difluoromethyl, trifluoromethyl, difluoroethyl and trifluoroethyl. More particular example is trifluoromethyl.

The term "heteroaryl", alone or in combination, denotes a monocyclic or polycyclic group comprising at least one aromatic ring, wherein the aromatic ring comprises at least one ring heteroatom. In some embodiments, the heteroatom is independently selected from the group consisting of N, O, and S. Unless otherwise specified, a heteroaryl group may comprise 5, 6, 7, 8, 9, 10, 11, or 12 ring atoms, comprising 1, 2, 3 or 4 heteroatoms selected from N, O and S, where ring atoms refer to the sum of carbon and heteroatoms in the one or more rings (e.g., be a 5-membered, 6-membered, 7-membered, 8-membered, 9-membered, 10-membered, 11-membered, or 12-membered heteroaryl). Examples of heteroaryl group include pyrrolyl, furanyl, oxazolyl, pyrazinyl, pyridazinyl, oxadiazolyl, isooxazol, pyrazol, triazolyl, and pyrimidinyl.

In the case of substituted heteroaryl, examples include 3-methyl-1,2,4-oxadiazol-5-yl, 3-methyl-1,2,4-triazol-1-yl, 3-methylisoxazol-5-yl, 3-methylpyrazol-1-yl, 4-methyloxazol-2-yl, 4-methylpyrazol-1-yl, 4-methyltriazol-2-yl, 5,5-dimethyl-4H-isoxazol-3-yl, 5-methyl-1,3,4-oxadiazol-2-yl, 5-methyloxazol-2-yl, 5-methylpyrazin-2-yl, and 5-methylpyrimidin-2-yl.

The term "heterocycloalkyl", alone or in combination, denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having at least one ring atoms in common. The heterocycloalkyl group may be saturated or unsaturated, and unless otherwise specified, may comprise 5, 6, 7, 8 or 9 ring atoms, where ring atoms refer to the sum of carbon and heteroatoms in the one or more rings (e.g., be a 5-membered, 6-membered, 7-membered, 8-membered or 9-membered heterocycloalkyl). Heterocycloalkyl may include groups comprising 1 to 5 ring heteroatoms, 1 to 4 heteroatoms, 1 to 3 ring heteroatoms, 1 or 2 ring heteroatoms, or 1 ring heteroatom. In some embodiments, the heterocycloalkyl comprises one ring, two rings, three rings, four rings, or more, for example as a polycyclic fused system. In some embodiments, heterocycloalkyl comprising multiple rings includes spirocyclic systems in which one or more rings comprise one or more heteratoms. Examples are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, dihydrofuryl, imidazolinyl, dihydro-oxazolyl, tetrahydro-pyridinyl, isooxazolyl, or dihydropyranyl.

In the case of substituted heterocycloalky, examples include methylisoxazolyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula I are the hydrochloride salts, methanesulfonic acid salts and citric acid salts.

"Pharmaceutically acceptable esters" means that compounds of general formula I may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula I, similar to the metabolically labile esters, which are capable of producing the parent compounds of general formula I in vivo, are within the scope of this invention.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention provides compounds according to formula I as described herein and pharmaceutically acceptable salts or esters thereof, in particular compounds according to formula I as described herein and pharmaceutically acceptable salts thereof, more particularly compounds according to formula I as described herein.

A particular embodiment of the present invention provides compounds according to formula I as described, wherein $R^1$ is selected from the group consisting of:
i) 5 or 6 member heteroaryl
ii) 5 or 6 member substituted heteroaryl
iii) 5 or 6 member heterocycloalkyl
iv) 5 or 6 member substituted heterocycloalkyl
wherein substituted heteroaryl or substituted heterocycloalkyl is substituted with one or more alkyl substituents;

$R^2$ is selected from the group consisting of
i) H,
ii) cyano,
iii) halogen,
iv) $C_{1-6}$-alkyl
v) halo-$C_{1-6}$-alkyl $R^3$ is selected from the groups consisting of
i) H,
ii) halogen,
iii) $C_{1-6}$-alkyl
iv) halo-$C_{1-6}$-alkyl or pharmaceutically acceptable salts.

A particular embodiment of the present invention provides compounds according to formula I as described herein, wherein $R^3$ is Halogen.

A further particular embodiment of the present invention provides compounds according to formula I as described herein, wherein $R^3$ is Cl.

A particular embodiment of the present invention provides compounds according to formula I as described herein, wherein $R^2$ is selected from the groups consisting of:
i) H,
ii) Cyano.

A particular embodiment of the present invention provides compounds according to formula I as described herein, wherein $R^1$ is selected from the group consisting of:
i) 5 or 6 member heteroaryl
ii) 5 or 6 member substituted heteroaryl
iii) 5 or 6 member substituted heterocycloalkyl
wherein substituted heteroaryl or substituted heterocycloalkyl is substituted with one or more alkyl substituents;

A particular embodiment of the present invention provides compounds according to formula I as described herein, wherein $R^1$ is selected from: 3-methyl-1,2,4-oxadiazol-5-yl, 3-methyl-1,2,4-triazol-1-yl, 3-methylisoxazol-5-yl, 3-methylpyrazol-1-yl, 4-methyloxazol-2-yl, 4-methylpyrazol-1-yl, 4-methyltriazol-2-yl, 5,5-dimethyl-4H-isoxazol-3-yl, 5-methyl-1,3,4-oxadiazol-2-yl, 5-methyloxazol-2-yl, 5-methylpyrazin-2-yl, 5-methylpyrimidin-2-yl, oxazol-2-yl, pyrazin-2-yl, and pyridazin-3-yl.

A particular embodiment of the present invention provides compounds according to formula I as described herein, wherein $R^1$ is selected from the group consisting of:
i) 5 or 6 member heteroaryl
ii) 5 or 6 member substituted heteroaryl
iii) 5 or 6 member substituted heterocycloalkyl
wherein substituted heteroaryl or substituted heterocycloalkyl is substituted with one or more alkyl substituents;

$R^2$ is selected from the groups consisting of:
i) H
ii) cyano $R^3$ is Halogen or pharmaceutically acceptable salts.

A more particular embodiment of the present invention provides compounds according to formula I as described herein, wherein $R^1$ is selected from the group consisting of:
i) 5 or 6 member heteroaryl
ii) 5 or 6 member substituted heteroaryl
iii) 5 or 6 member substituted heterocycloalkyl
wherein substituted heteroaryl or substituted heterocycloalkyl is substituted with one or more alkyl substituents;

$R^2$ is selected from the groups consisting of:
i) H
ii) cyano $R^3$ is Cl

A most particular embodiment of the present invention provides compounds according to formula I as described herein, wherein $R^1$ is selected from the group consisting of: 3-methyl-1,2,4-oxadiazol-5-yl, 3-methyl-1,2,4-triazol-1-yl, 3-methylisoxazol-5-yl, 3-methylpyrazol-1-yl, 4-methyloxazol-2-yl, 4-methylpyrazol-1-yl, 4-methyltriazol-2-yl, 5,5-dimethyl-4H-isoxazol-3-yl, 5-methyl-1,3,4-oxadiazol-2-yl, 5-methyloxazol-2-yl, 5-methylpyrazin-2-yl, 5-methylpyrimidin-2-yl, oxazol-2-yl, pyrazin-2-yl, and pyridazin-3-yl;

$R^2$ is selected from the groups consisting of:

i) H ii) cyano $R^3$ is Cl

Particular examples of compounds of formula I as described herein are selected from N-(5-chloro-2,3-dihydro-1H-inden-2-yl)-5-(3-methyl-1,2,4-oxadiazol-5-yl)pyrimidin-2-amine;

N-(5-chloro-2,3-dihydro-1H-inden-2-yl)-5-(5-methyl-1,3,4-oxadiazol-2-yl)pyrimidin-2-amine;

N-(5-chloro-2,3-dihydro-1H-inden-2-yl)-5-(4-methyloxazol-2-yl)pyrimidin-2-amine;

N-(5-chloro-2,3-dihydro-1H-inden-2-yl)-5-(3-methylisoxazol-5-yl)pyrimidin-2-amine;

N-(5-chloro-2,3-dihydro-1H-inden-2-yl)-5-(4-methyl-1H-pyrazol-1-yl)pyrimidin-2-amine;

N-(5-chloro-2,3-dihydro-1H-inden-2-yl)-5-(3-methyl-1H-pyrazol-1-yl)pyrimidin-2-amine;

N-(5-chloro-2,3-dihydro-1H-inden-2-yl)-5-(4-methyltriazol-2-yl)pyrimidin-2-amine;

N-(5-chloro-2,3-dihydro-1H-inden-2-yl)-5-(5-methyloxazol-2-yl)pyrimidin-2-amine;

(S or R)—N-(5-chloro-2,3-dihydro-1H-inden-2-yl)-5-(3-methyl-1,2,4-oxadiazol-5-yl)pyrimidin-2-amine;

(R or S)—N-(5-chloro-2,3-dihydro-1H-inden-2-yl)-5-(3-methyl-1,2,4-oxadiazol-5-yl)pyrimidin-2-amine;

N-(5-chloro-2,3-dihydro-1H-inden-2-yl)-5-(5,5-dimethyl-4,5-dihydroisoxazol-3-yl)pyrimidin-2-amine;

(S)-6-chloro-2-((5-(3-methyl-1,2,4-oxadiazol-5-yl)pyrimidin-2-yl)amino)-2,3-dihydro-1H-indene-4-carbonitrile;

(S)-6-chloro-2-((5-(3-methylisoxazol-5-yl)pyrimidin-2-yl)amino)-2,3-dihydro-1H-indene-4-carbonitrile;

(S)-6-chloro-2-((5-(4-methyloxazol-2-yl)pyrimidin-2-yl)amino)-2,3-dihydro-1H-indene-4-carbonitrile;

(S)-6-chloro-2-((5-(5-methyloxazol-2-yl)pyrimidin-2-yl)amino)-2,3-dihydro-1H-indene-4-carbonitrile;

(S)-6-chloro-2-((5-(5-methylpyrazin-2-yl)pyrimidin-2-yl)amino)-2,3-dihydro-1H-indene-4-carbonitrile;

(S)-6-chloro-2-((5-methyl-[2,5"-bipyrimidin]-2"-yl)amino)-2,3-dihydro-1H-indene-4-carbonitrile;

(S)-6-chloro-2-[[5-(3-methyl-1,2,4-triazol-1-yl)pyrimidin-2-yl]amino]-2,3-dihydro-1H-indene-4-carbonitrile;

and pharmaceutically acceptable salts thereof.

Processes for the manufacture of compounds of formula I as described herein are an object of the invention.

The present compounds of formula I and their pharmaceutically acceptable salts can be prepared by methods known in the art, for example, by processes described below, which process comprises a) reacting a compound of formula

II

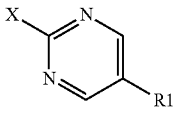

with a compound of formula

III

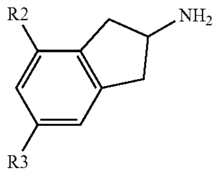

in the presence of a base like N,N-diisopropylethylamine to provide a compound of formula

I

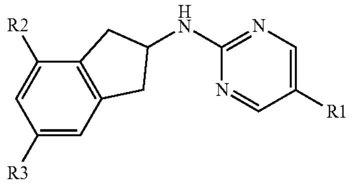

Wherein X is an halogen like Cl or a thiomethyl group and the substituents are as defined above, with the proviso that when X is a thiomethyl group, this group is transformed to the corresponding methylsulfone group with an oxidant like 3-chloroperbenzoic acid prior to reaction with III, or reacting a compound of formula

R1-X IV with a compound of formula

V

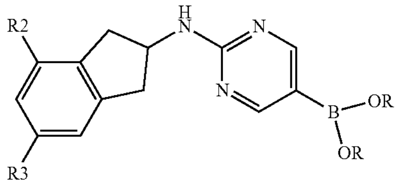

in the presence of a catalyst like [1,1'-bis(diphenylphosphino)ferrocene] dichloropalladium (II) and a base like potassium carbonate to provide a compound of formula

I

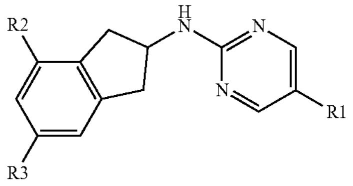

Wherein X is a halogen like Cl or Br and the substituents are as defined above.

b) reacting a compound of formula

R1-H VI with a compound of formula

VII

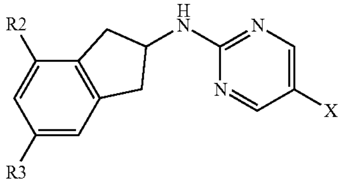

in the presence of a catalyst like copper (I) iodide, a chelating agent like 8-hydroxyquinoline and a base like potassium carbonate to provide a compound of formula

I

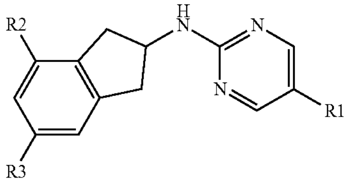

Wherein X is a halogen like Cl or Br and the substituents are as defined above.

c) reacting a compound of formula

R1-M VIII with a compound of formula

VII

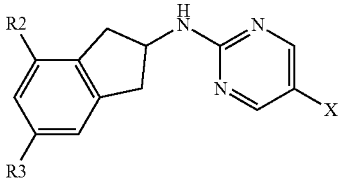

in the presence of a catalyst like [1,1'-bis(diphenylphosphino)ferrocene] dichloropalladium (II) and a base like potassium or cesium carbonate when M is —$B(OR)_2$ or in the presence of a catalyst like bis(triphenylphospine)palladium(II) chloride when M is —$Sn(nBu)_3$ to provide a compound of formula

I

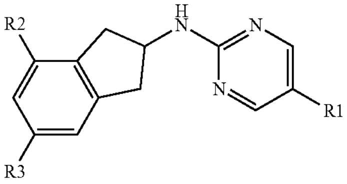

Wherein X is a halogen like Cl or Br and the substituents are as defined above.

d) transforming a compound of formula

IX

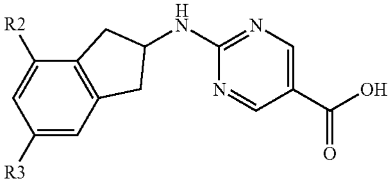

to a compound of formula

I

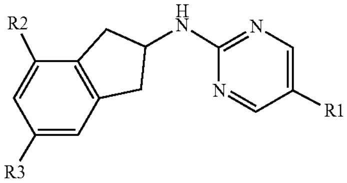

Wherein the substituents are as defined above.

The compounds of formula I may be prepared in accordance with the process variant described above and with the following schemes 1-3. The starting materials are commercially available or may be prepared in accordance with known methods.

Scheme 1

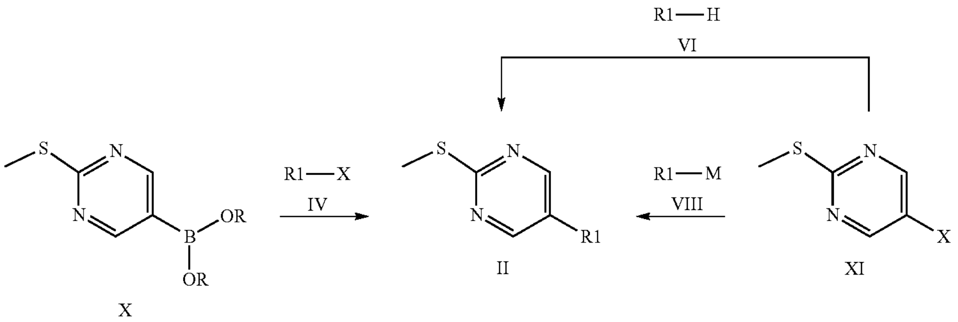

-continued

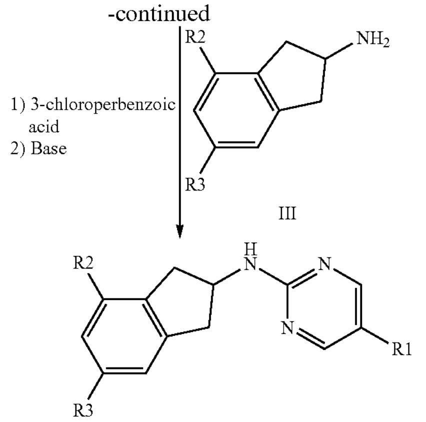

III

I

X: halogen
M: $B(OR)_2$ or $Sn(nBul)_3$

Compounds of general formula I can be prepared by reacting a thiomethyl derivative II with an oxidant like 3-chloroperbenzoic acid to transform II into its corresponding methyl sulfone derivative which is then reacted with the amine derivative III. The thiomethyl derivative of formula II can be prepared by reaction of a boronic ester X with an halogenated derivative IV in the presence of a catalyst like [1,1'-bis(diphenylphosphino)ferrocene] dichloropalladium (II) and a base like potassium carbonate. Alternatively, II can be prepared by reaction of an halogenated thiomethyl derivative XI with an organometallic reagent VIII in the presence of a catalyst like [1,1'-bis(diphenylphosphino)ferrocene] dichloropalladium (II) and a base like potassium or cesium carbonate when M is $B(OR)_2$ or in the presence of a catalyst like bis(triphenylphospine)palladium(II) chloride when M is $—Sn(nBu)_3$. II can also be prepared by reaction of XI with VI in the presence of a catalyst like copper (I) iodide, a chelating agent like 8-hydroxyquinoline and a base like potassium carbonate.

Scheme 2

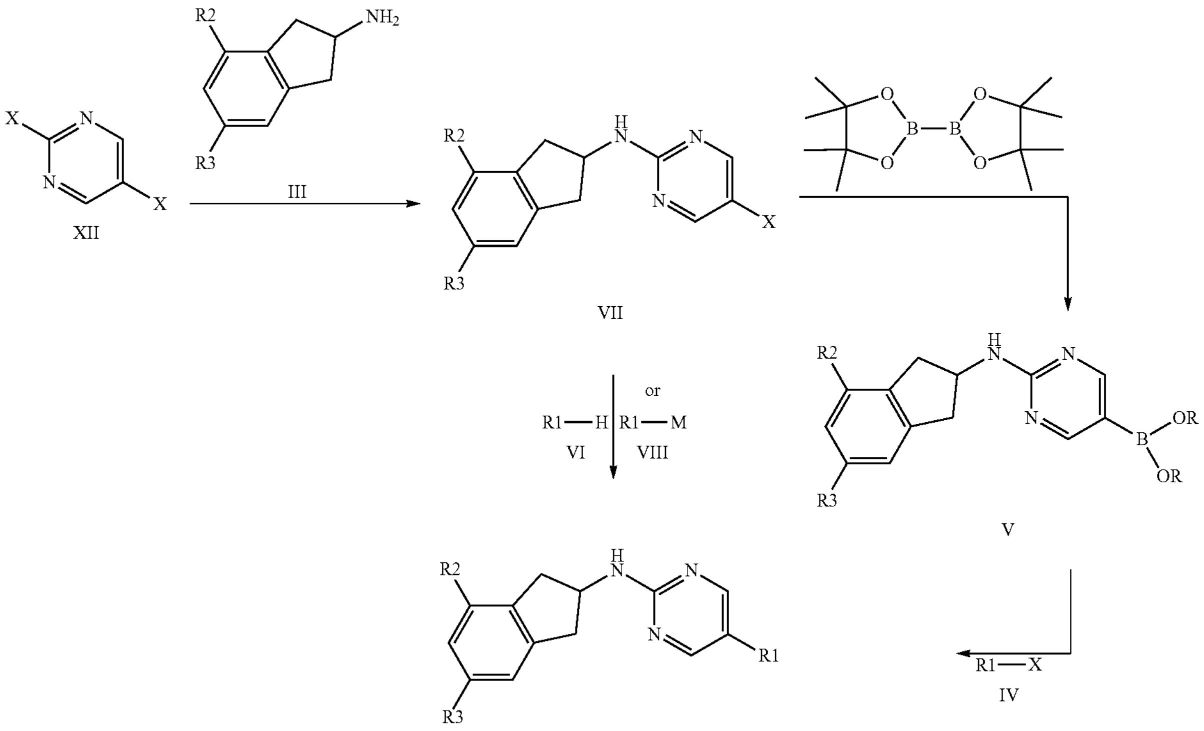

XII

VII

VI

VIII

V

IV

I

X: halogen
M: $B(OR)_2$ or $Sn(nBul)_3$

Compounds of general formula I can be prepared by reacting halogenated derivative VII with R1-H (VI) in the presence of a catalyst like copper (I) iodide, a chelating agent like 8-hydroxyquinoline and a base like potassium carbonate, or by reacting VII with organometallic reagent VIII in the presence of a catalyst like [1,1'-bis(diphenylphosphino)ferrocene] dichloropalladium (II) and a base like potassium or cesium carbonate when M is —B(OR)$_2$ or in the presence of a catalyst like bis(triphenylphospine)palladium(II) chloride when M is —Sn(nBu)$_3$. Alternatively, I can be prepared by reacting boronic ester V with an halogenated derivative IV in the presence of a catalyst like [1,1'-bis(diphenylphosphino)ferrocene] dichloropalladium (II) and a base like potassium carbonate. V can be prepared from halogenated derivative VII in the presence of bis(pinacolato)diboron, a catalyst like [1,1'-bis(diphenylphosphino)ferrocene] dichloropalladium (II) and a base like potassium acetate. VII can be prepared by reacting halogenated derivative XII with amine III in the presence of a base like N,N-diisopropylethylamine.

Scheme 3

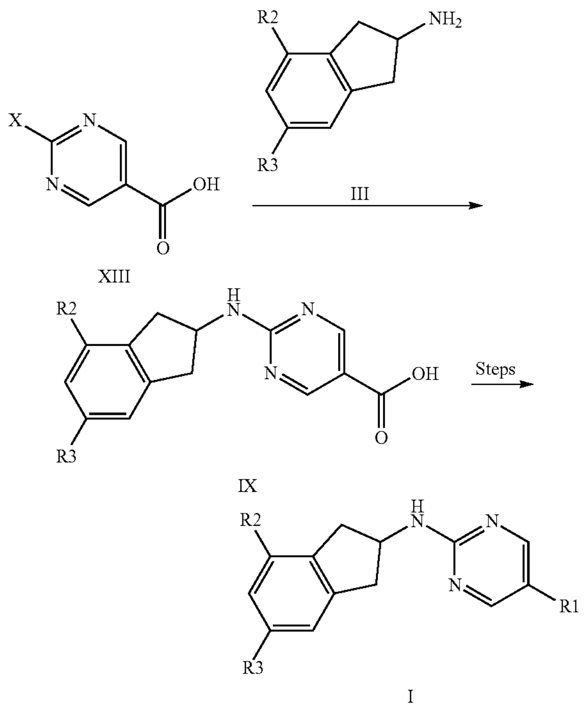

XIII

IX

I

X: halogen

Compounds of general formula I can be prepared from acid IX by method known in the art. IX can be prepared by reaction halogenated reagent XIII with amine derivative III in the presence of a base like N,N-diisopropylethylamine.

Also an object of the present invention is a compound according to formula I as described herein for use as a therapeutically active substance.

Likewise an object of the present invention is a pharmaceutical composition comprising a compound according to formula I as described herein and a therapeutically inert carrier.

An object of the invention is the use of a compound according to formula I as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

The present invention also relates to the use of a compound according to formula I as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula I as described herein for the treatment or prophylaxis of renal conditions, liver conditions and fibrotic diseases.

A particular embodiment of the present invention is a compound according to formula I as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula I as described herein for the treatment or prophylaxis of renal conditions, liver conditions and fibrotic diseases.

The present invention also relates to the use of a compound according to formula I as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula I as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula I as described herein.

Also an object of the invention is a method for the treatment or prophylaxis of renal conditions, liver conditions and fibrotic diseases, which method comprises administering an effective amount of a compound according to formula I as described herein.

Also an embodiment of the present invention provides compounds of formula I as described herein, when manufactured according to any one of the described processes.

Assay Procedures

Production of Human Full Length ATX, with and without His Tag

Autotaxin (ATX-ENPP2) cloning: cDNA was prepared from commercial human hematopoietic cells total RNA and used as template in overlapping PCR to generate a full length human ENPP2 ORF with or without a 3'-6×His tag. These full-length inserts were cloned into the pcDNA3.1V5-His TOPO (Invitrogen) vector. The DNA sequences of several single clones were verified. The DNA from a correct full-length clone was used to transfect Hek293 cells for verification of protein expression. The sequence of the encoded ENPP2 conforms to Swissprot entry Q13822, with or without the additional C-terminal 6×His tag.

ATX Fermentation: Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification. ATX Purification: 20 liter of culture supernatant were conditioned for ultrafiltration by adding Brij 35 to a final concentration of 0.02% and by adjusting the pH to 7.0 using 1 M HC1. Then the supernatant was first microfiltred through a 0.2 pm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, NiSO4 was added to a final concentration of 1 mM. The cleared supernatant was then applied to a HisTrap column (GE Healthcare) previously equilibrated in 50 mM Na2HPO4 pH 7.0, 0.5 M NaCl, 10% glycerol, 0.3% CHAPS, 0.02% NaN3. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% NaN3. Final yield of protein after purification was 5-10 mg ATX per liter of culture supernatant. The protein was stored at −80° C.

Human ATX Enzyme Inhibition Assay

To identify inhibitors of the human Autotaxin (ATX) enzyme an in-vitro biochemical profiling assay has been developed using lysophosphatidylcholine (LPC) as substrate and recombinant enzyme. ATX activity is assayed via a coupled enzyme format where choline produced from LPC hydrolysis is converted to hydrogen peroxide by choline oxidase (CO). Hydrogen peroxide is in turn used as a co-substrate by horseradish peroxidase (HRP) to oxidise Amplex Red® and generate the red-fluorescent product, Resorufin.

Materials/Reagents 500 mM Tris-HCl pH 8.0; 1M NaCl; 250 mM $CaCl_2$; 250 mM KCl; 250 mM $MgCl_2$; 10% Triton X-100 in $H_2O$.

Assay Buffer 50 mM Tris-HCl (pH 8.0); 120 mM NaCl; 20 mM $CaCl_2$; 5 mM KCl; 1 mM $MgCl_2$; 0.01% Triton X-100, sterile-filtered and stored at 4° C.

Reagent Dilution Buffer 50 mM Tris-HCl (pH 8.0); 150 mM NaCl human Autotaxin (hATX): 0.97 mg/ml (9.718 μM) Molecular weight 99817. Working solution of 1.5 μM used in this assay.

100 mM 18:1 LPC dissolved in reagent dilution-buffer.

500 U/ml Choline Oxidase in reagent dilution buffer.

2540 U/ml Horseradish Peroxidase, in reagent dilution buffer (10.95 mg/ml).

20 mM Amplex Red (10-Acetyl-3,7-dihydroxy-phenoxazin) in DMSO.

Reaction Plate

Black, 384-well plate, black with clear bottom, non-treated surface.

Test compounds are received pre-diluted in DMSO as an 11-point concentration-response (0.5 mM highest concentration; 1 in 3.162 dilution). Test compounds are pre-diluted 1:1 (10 μL compound+10 μL assay buffer) in a 96-well conical bottomed plate prior to use.

Procedure

ATX is diluted to 2.2 nM in assay buffer. Choline oxidase and horseradish peroxidase are diluted to 7.3 U/ml and 14.7 U/ml, respectively. 18:1 LPC and Amplex Red® are diluted to 110 μM and 183.3 μM, respectively (solution protected from light). 2.2 μL of compound pre-dilution or 50% DMSO is added to the reaction plate followed by 25 μL of ATX or assay buffer (negative control). Assay plate is mixed and incubated at room temperature for 10 mins. 15 μL of choline oxidase/horseradish peroxidase is then added. To initiate the reaction 15 μL of LPC 18:1/Amplex Red is added. Assay plate is mixed and incubated at room temperature in the dark. Fluorescence is measured at 5 mins (for background subtraction) and 90 mins.

Final Assay Concentrations:

hATX: 1 nM

18:1 LPC: 30 μM

Choline Oxidase: 2 U/ml

Horse Radish Peroxidase: 4 U/ml

Amplex Red®: 50 μM

DMSO: 2%

Fluorescence at 5-minutes is subtracted from the 90-minute end point data and normalized with respect to the positive control. $IC_{50}$ values are calculated.

Results in the enzymatic ATX inhibition assay are provided for compounds of formula I.

TABLE

| Example | ATX IC50 [□M] |
|---|---|
| 1 | 0.108 |
| 2 | 0.221 |
| 3 | 0.108 |
| 4 | 0.038 |

TABLE-continued

| Example | ATX IC50 [□M] |
|---|---|
| 5 | 0.177 |
| 6 | 0.163 |
| 7 | 0.217 |
| 8 | 0.18 |
| 9 | 0.235 |
| 10 | 0.16 |
| 11 | 0.251 |
| 12 | 0.139 |
| 13 | 0.217 |
| 14 | 0.216 |
| 15 | 0.009 |
| 16 | 0.004 |
| 17 | 0.008 |
| 18 | 0.004 |
| 19 | 0.01 |
| 20 | 0.014 |
| 21 | 0.012 |

Compounds of formula I and their pharmaceutically acceptable salts or esters thereof as described herein have $IC_{50}$ values between 0.004 μM and 0.251 μM. These results have been obtained by using the enzymatic assay described above.

The compounds of formula I and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula I and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Intermediates A

Intermediate A1: 5-chloro-2,3-dihydro-1H-inden-2-amine hydrochloride

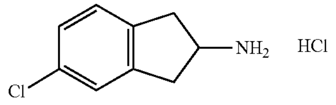 [SMILES: NC1Cc2ccc(Cl)cc2C1 ; Cl]

Intermediate A1 is commercial (CAS: 73536-86-4)

Intermediate A2: (S)-6-chloro-4-cyano-2,3-dihydro-1H-inden-2-aminium chloride

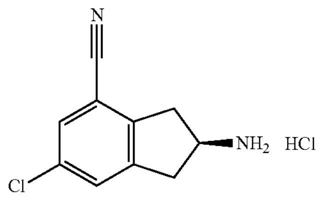 [SMILES: N#Cc1cc(Cl)cc2c1C[C@@H](N)C2 ; Cl]

Step 1: 4-(4,4,5,5-tetramethyl-1,3,2-dioxaborolan-2-yl)-2,3-dihydro-1H-inden-2-yl)carbamate

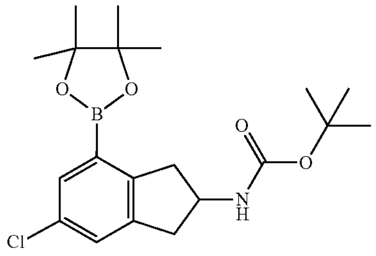 [SMILES: CC(C)(C)OC(=O)NC1Cc2cc(Cl)cc(B3OC(C)(C)C(C)(C)O3)c2C1]

4,4,4',4',5,5,5',5'-octamethyl-2,2'-bi(1,3,2-dioxaborolane) (2.42 g, 9.34 mmol), (1,5-cyclooctadiene)(methoxy) iridium (I) dimer (309 mg, 467 μmol), tert-butyl (5-chloro-2,3-dihydro-1H-inden-2-yl)carbamate (2.50 g, 9.34 mmol, CAS: 1934835-81-0) and 3,4,7,8-tetramethyl-1,10-phenanthroline (221 mg, 934 μmol) were combined in a microwave vial (dried using high vacuum and flushed with Argon) and were suspended in dry THF (10 ml). On mixing these reagents, the suspension turned dark green. Argon was bubbled through the suspension for 10 min. The reaction mixture was heated to 80° C. and stirred for 15 h (turned dark violet). The reaction mixture was filtered through sintered glass and concentrated in vacuo. The crude material was purified by flash chromatography over silica gel using a gradient ethylacetate/heptane 0-30% to provide the title compound as an off-white solid (2.30 g, 63% yield). MS (ESI): m/z=294.2 $[M\text{-}Boc+H]^+$

Step 2: Tert-butyl (6-chloro-4-hydroxy-2,3-dihydro-1H-inden-2-yl)carbamate

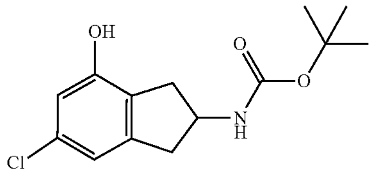 [SMILES: CC(C)(C)OC(=O)NC1Cc2cc(Cl)cc(O)c2C1]

4-(4,4,5,5-tetramethyl-1,3,2-dioxaborolan-2-yl)-2,3-dihydro-1H-inden-2-yl)carbamate (850 mg, 1.84 mmol) was dissolved in THF (5.56 ml) and water (556 μl) and sodium perborate monohydrate (549 mg, 5.51 mmol) was added. The reaction was stirred at rt for 18 hours. The solvent was evaporated and the residue was taken up in water and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ehylacetate/heptane 0-50% to provide the title compound as a off-white solid (220 mg, 42% yield). MS (ESI): m/z=282.2 $[M-H]^+$ Step 3: 2-((tert-butoxycarbonyl)amino)-6-chloro-2,3-dihydro-1H-inden-4-yl trifluoromethanesulfonate

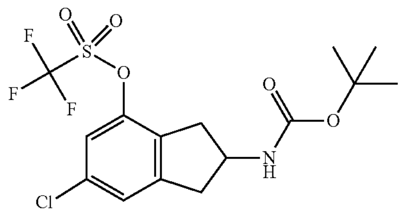 [SMILES: CC(C)(C)OC(=O)NC1Cc2cc(Cl)cc(OS(=O)(=O)C(F)(F)F)c2C1]

Tert-butyl (6-chloro-4-hydroxy-2,3-dihydro-1H-inden-2-yl)carbamate (50 mg, 176 μmol) was dissolved in dry DCM (705 μl) and triethylamine (19.6 mg, 27 μl, 194 μmol) was added. To this stirred solution, 1,1,1-trifluoro-N-phenyl-N-((trifluoromethyl)sulfonyl)methanesulfonamide (69.2 mg, 194 μmol) was added. The reaction was stirred at rt for 3 hours, poured into water and extracted with EtOAc. The layers were separated and the aqueous layer was extracted twice with EtOAc. The combined organic layers were washed with brine, dried over anhydrous sodium sulfate and evaporated to dryness. The crude product was subjected to flash chromatography over silica gel using a gradient ehylacetate/heptane 0-50% to provide the title compound as a white solid (42 mg, 57% yield). MS (ESI): m/z=414.1 $[M-H]^+$ Step 4: tert-butyl (6-chloro-4-cyano-2,3-dihydro-1H-inden-2-yl)carbamate

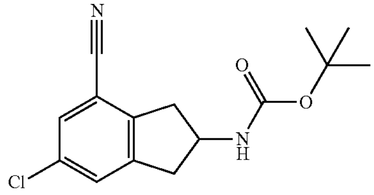 [SMILES: CC(C)(C)OC(=O)NC1Cc2cc(Cl)cc(C#N)c2C1]

2-((tert-butoxycarbonyl)amino)-6-chloro-2,3-dihydro-1H-inden-4-yl trifluoromethanesulfonate (60 mg, 144 μmol), zinc cyanide (9.32 mg, 79.4 μmol) and tetrakis (triphenylphosphine) palladium (0) (16.7 mg, 14.4 μmol) were dissolved in dry DMF (721 μl) and Argon was bubbled through the reaction for 5 minutes. Following, the reaction was heated to 110° C. for 2 hours. The reaction was poured into LiCl 10% and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ethylacetate/heptane 0-50% to provide the title compound as a white solid (24 mg, 57% yield). MS (ESI): m/z=237.1 $[M-tBu]^+$ Step 5: (S)-tert-butyl (6-chloro-4-cyano-2,3-dihydro-1H-inden-2-yl)carbamate

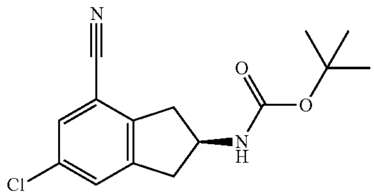 [SMILES: CC(C)(C)OC(=O)N[C@H]1Cc2cc(Cl)cc(C#N)c2C1]

tert-butyl (6-chloro-4-cyano-2,3-dihydro-1H-inden-2-yl) carbamate (65 mg, 222 μmol) was separated on a chiral column (OZ-H, 12 nm, 5 μm, 250×4.6 mm) on SFC condition to provide the title compound as a white solid (32 mg, 49.2% yield, 96% ee, second eluting enantiomer, retention time: 6.6 min.). MS (ESI) m/z: 237.1 $[M-tBu]^+$ Step 6: (S)-6-chloro-4-cyano-2,3-dihydro-1H-inden-2-aminium chloride

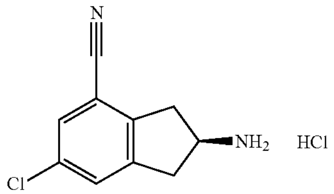 [SMILES: N#Cc1cc(Cl)cc2c1C[C@@H](N)C2 ; Cl]

A solution of (S)-tert-butyl-(6-chloro-4-cyano-2,3-dihydro-1H-inden-2-yl)carbamate; (300 mg, 1.02 mmol,) and HCl 4 M in dioxane (3.84 ml, 15.4 mmol) in dioxane (2 ml) was stirred at rt for 15 h. The resulting suspension was concentrated in vacuo to provide the title compound (237 mg, 100% yield) as a white solid. MS (ESI): m/z=193.1 [M+H]+

Intermediates B

Intermediate B1: 2-((5-chloro-2,3-dihydro-1H-inden-2-yl)amino)pyrimidine-5-carboxylic acid

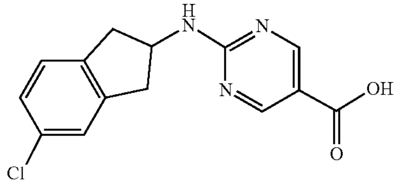 [SMILES: O=C(O)c1cnc(NC2Cc3ccc(Cl)cc3C2)nc1]

To a mixture of 5-chloro-2,3-dihydro-1H-inden-2-amine hydrochloride (709 mg, 3.48 mmol, intermediate A1) in N-Methyl-2-pyrrolidinone (5 ml) at room temperature under argon, were added 2-chloropyrimidine-5-carboxylic acid (551 mg, 3.48 mmol) and potassium carbonate (2.4 g, 17.4 mmol). The mixture was stirred at 80° C. for 18 hours. The reaction mixture was cooled to room temperature and poured into 2 M HCl and ethyl acetate. The resulting suspension was filtered. both layers of the filtrate were separated and the aqueous layer was extracted twice with ethyl acetate. The combined organic layers were dried over sodium sulfate and evaporated. The crude material (964 mg) was purified by flash chromatography over silica gel using a gradient ethylacetate/heptane 0-100% to provide the title compound as a light brown solid (491 mg, 49% yield). MS (ESI): m/z=288.1 [M−H]$^+$ Intermediate B2: 5-bromo-N-(5-chloro-2,3-dihydro-1H-inden-2-yl)pyrimidin-2-amine

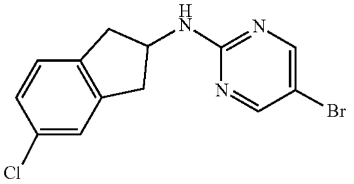 [SMILES: Clc1ccc2c(c1)CC(Nc1ncc(Br)cn1)C2]

To a mixture of 5-bromo-2-chloropyrimidine (569 mg, 2.94 mmol) in acetonitrile (5 ml) under argon at room temperature were added 5-chloro-2,3-dihydro-1H-inden-2-amine hydrochloride (500 mg, 2.45 mmol, intermediate A1) and N,N-diisopropylethylamine (950 mg, 1.28 ml, 7.35 mmol). The mixture was stirred at 50° C. for 5.5 hours and was quenched with water. Ethyl acetate was added both layers were separated and the aqueous one was extracted twice with ethyl acetate. The combined organic layers were dried over sodium sulfate and evaporated. The crude material (813 mg) was purified by flash chromatography over silica gel using a gradient ethylacetate/heptane 0-30% to provide the title compound as an offwhite solid (246 mg, 31% yield). MS (ESI): m/z=326.1 [M+H]$^+$ Intermediate B3: N-(5-chloro-2,3-dihydro-1H-inden-2-yl)-5-(4,4,5,5-tetramethyl-1,3,2-dioxaborolan-2-yl)pyrimidin-2-amine

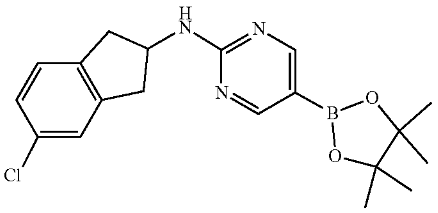 [SMILES: CC1(C)OB(c2cnc(NC3Cc4ccc(Cl)cc4C3)nc2)OC1(C)C]

A mixture of 5-bromo-N-(5-chloro-2,3-dihydro-1H-inden-2-yl)pyrimidin-2-amine; (200 mg, 616 µmol, intermediate B2), bis(pinacolato)diboron (319 mg, 1.23 mmol), potassium acetate (67.2 mg, 678 µmol) and 1,1'-Bis(diphenylphosphino)ferrocene-Palladium(II) Dichloride Dichloromethane Complex (25.2 mg, 30.8 µmol) in dioxane (4 ml) was heated to 90° C. and stirred for 15 h. The reaction mixture was poured into water and extracted twice with EtOAc. The combined organic layers were dried over sodium sulfate and concentrated in vacuo. The crude material was purified by flash chromatography over silica gel using a gradient ethylacetate/heptane 0-100% to provide the title compound as an orange solid (175 mg, 76% yield). MS (ESI): m/z=372.2 [M+H]$^+$ Intermediate B4: 3-(2-chloropyrimidin-5-yl)-5,5-dimethyl-4,5-dihydroisoxazole

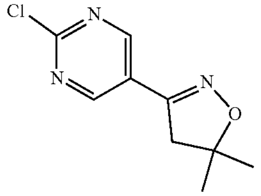

Step 1: (Z)-2-chloro-N-hydroxypyrimidine-5-carbimidoyl chloride

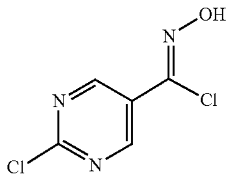 [SMILES: O/N=C(\Cl)c1cnc(Cl)nc1]

A solution of (E)-2-chloropyrimidine-5-carbaldehyde oxime (500 mg, 3.17 mmol, CAS: 1280538-48-8) in DMF (5 ml) was cooled to 0° C. n-Chlorosuccinimide (432 mg, 3.17 mmol) was added portionwise. The reaction mixture was stirred allowed to warm to rt and stirred for 5 h. The resulting suspension was concentrated in vacuo. The residue was triturated with dichloromethane, filtered through sintered glass, washed with diethylether and dried in vacuo to provide the title compound as an off-white solid (214 mg, 35% yield). MS (ESI): m/z=192.0 [M+H]$^+$ Step 2: 3-(2-chloropyrimidin-5-yl)-5,5-dimethyl-4,5-dihydroisoxazole

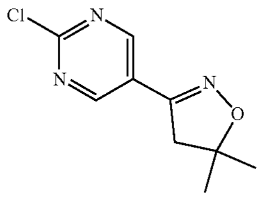

(Z)-2-chloro-N-hydroxypyrimidine-5-carbimidoyl chloride (100 mg, 521 µmol) was dissolved in N,N-dimethylformamide (1 ml). The mixture was cooled to 0° C., and 2-methylprop-1-ene (29.2 mg, 521 µmol) was bubbled through the suspension for 2 minutes. After that, a solution of triethylamine (116 mg, 159 µl, 1.15 mmol) in N,N-dimethylformamide (100 µl) was added dropwise. The reaction mixture was stirred at 0° C. for 40 minutes. The reaction was carefully quenched with ice-cold water. Ethyl acetate was added. Both layers were separated and the aqueous one was extracted twice with ethyl acetate. The combined organic layers were dried over sodium sulfate and evaporated. The crude orange oil was purified with flash column chromatography over silica gel using a gradient ethylacetate/ heptane 0-40% to provide the title compound as a white solid (9 mg, 8% yield). MS (ESI): m/z=212.1 [M+H]+

Intermediate B5: 3-methyl-5-(2-(methylthio)pyrimidin-5-yl)-1,2,4-oxadiazole

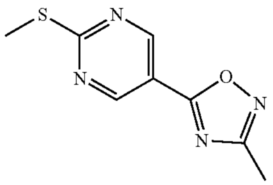

To a suspension of 2-(methylthio)pyrimidine-5-carboxylic acid (1 g, 5.88 mmol) in N,N-dimethylformamide dry (12.5 ml) under nitrogen at room temperature, was added 1,1'-carbonyldiimidazole (1.08 g, 6.46 mmol). The reaction mixture was stirred at room temperature for 30 minutes. Then (E)-N'-hydroxyacetimidamide (504 mg, 6.46 mmol) was added. The reaction mixture was heated to 115° C. for 19 hours. The reaction mixture was cooled to room temperature and the solvent was removed in vacuo. The crude solid was dissolved in dichloromethane and a small amount of methanol.

The resulting suspension was filtered. The mother liquor was purified with flash column chromatography over silica gel using a gradient ethylacetate/heptane 0-20% to provide the title compound as a white solid (147 mg, 12% yield). MS (ESI): m/z=209.1 [M+H]+

Intermediate B6: 3-methyl-5-(2-(methylthio)pyrimidin-5-yl)isoxazole

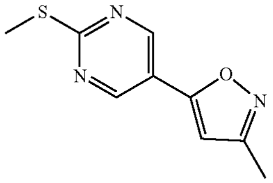

To a yellow solution of 5-bromo-2-(methylthio)pyrimidine (150 mg, 731 μmol) in 1,4-dioxane (1.5 ml) and water (750 μl) under nitrogen, were added 3-methyl-5-(4,4,5,5-tetramethyl-1,3,2-dioxaborolan-2-yl)isoxazole (322 mg, 1.46 mmol) and cesium carbonate (715 mg, 2.19 mmol). The mixture was degassed for 15 minutes. Then 1,1-bis(diphenylphosphino)ferrocenedichloropalladium(II) (59.7 mg, 73.1 μmol) was added. The reaction mixture was stirred in a microwave at 80° C. for 45 minutes (15 minutes). The reaction mixture was quenched with water. Ethyl acetate and brine were added. Both layers were separated and the aqueous one was extracted twice with ethyl acetate. The combined organic layers were dried over sodium sulfate and evaporated. The crude brown semi-solid (292 mg) was purified with flash column chromatography over silica gel using a gradient ethylacetate/heptane 0-20% to provide the title compound as a light brown solid (45 mg, 30% yield). MS (ESI): m/z=208.1 [M+H]+

Intermediate B7: 4-methyl-2-(2-(methylthio)pyrimidin-5-yl)oxazole

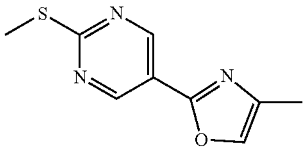

To a solution of 5-bromo-2-(methylthio)pyrimidine (150 mg, 731 μmol) in acetonitrile (5 ml) under nitrogen at room temperature, were added 4-methyl-2-(tributylstannyl)oxazole (991 mg, 2.66 mmol) and bis(triphenylphospine)palladium(II) chloride (69.3 mg, 98.7 μmol). The reaction mixture was stirred at 80° C. for 18 hours. The resulting dark mixture was cooled to room temperature and evaporated in vacuo. The crude dark residue was purified with flash column chromatography over silica gel using a gradient ethylacetate/heptane 0-30% to provide the title compound as a light brown solid (73 mg, 48% yield). MS (ESI): m/z=208.1 [M+H]+

Intermediate B8: 5-methyl-2-(2-(methylthio)pyrimidin-5-yl)oxazole

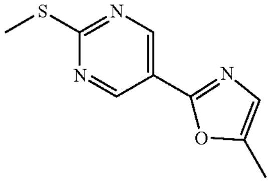

To a solution of 2-(methylthio)-5-(4,4,5,5-tetramethyl-1,3,2-dioxaborolan-2-yl)pyrimidine (1 g, 3.89 mmol, CAS: 940284-18-4) in dioxane (10 ml) and water (1 ml) under nitrogen at room temperature, were added 2-bromo-5-methyloxazole (994 mg, 5.83 mmol) and potassium carbonate anhydrous (1.07 g, 7.77 mmol). Argon was bubbled inside the reaction for 10 minutes. After that, [1,1'-bis(diphenylphosphino)ferrocene] dichloropalladium (II) (284 mg, 389 μmol) was added. The reaction mixture was stirred at 110° C. for 4.5 hours. The mixture was cooled to room temperature. Water and ethyl acetate were added. Both layers were separated and the aqueous one was extracted twice with ethyl acetate. The combined organic layers were dried over sodium sulfate and evaporated. The crude brown semi-solid (2.49 g) was purified with flash column chromatography over silica gel using a gradient ethylacetate/heptane 0-40% to provide the title compound as a light brown solid (422 mg, 52% yield). MS (ESI): m/z=208.1 [M+H]+

Intermediate B9: 5-(5-methylpyrazin-2-yl)-2-(methylthio)pyrimidine

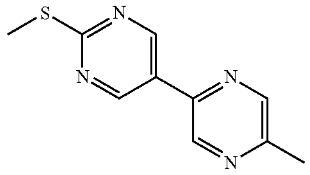

The title compound was prepared in analogy to intermediate B8 from 2-(methylthio)-5-(4,4,5,5-tetramethyl-1,3,2-dioxaborolan-2-yl)pyrimidine, CAS: 940284-18-4) and 2-bromo-5-methylpyrazine as an off-white solid. MS (ESI): m/z=219.1 $[M+H]^+$ Intermediate B10: 5-methyl-2'-(methylthio)-2,5'-bipyrimidine

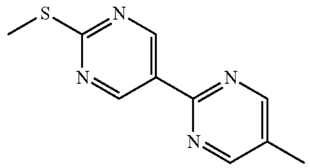

The title compound was prepared in analogy to intermediate B8 from 2-(methylthio)-5-(4,4,5,5-tetramethyl-1,3,2-dioxaborolan-2-yl)pyrimidine, CAS: 940284-18-4) and 2-chloro-5-methylpyrimidine as an off-white solid. MS (ESI): m/z=219.1 $[M+H]^+$ Intermediate B11: 5-(3-methyl-1H-1,2,4-triazol-1-yl)-2-(methylthio)pyrimidine

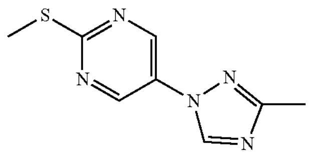

To a mixture of 5-bromo-2-(methylthio)pyrimidine (500 mg, 2.44 mmol) in DMSO (9 ml) were added 3-methyl-1H-1,2,4-triazole (427 mg, 4.88 mmol), copper (I) iodide (92.9 mg, 488 μmol), 8-hydroxyquinoline (142 mg, 975 μmol) and potassium carbonate (674 mg, 4.88 mmol). The mixture was stirred in a microwave oven for 15 minutes at 130° C., then it was stirred in a microwave oven for 45 minutes at 150° C. The mixture was quenched with NH4Cl solution (20%), then ethyl acetate was added, the resulting suspension was filtered and both layers of the filtrate were separated. The aqueous layer was extracted twice with ethyl acetate. The combined organic layers were dried over sodium sulfate and concentrated. The crude material (1.45 g) was purified by flash chromatography over silica gel using a gradient ethylacetate/heptane 0-60% to provide the title compound as a yellow solid (56 mg, 10% yield). MS (ESI): m/z=208.1 $[M+H]^+$

EXAMPLES

Example 1: N-(5-chloro-2,3-dihydro-1H-inden-2-yl)-5-(3-methyl-1,2,4-oxadiazol-5-yl)pyrimidin-2-amine

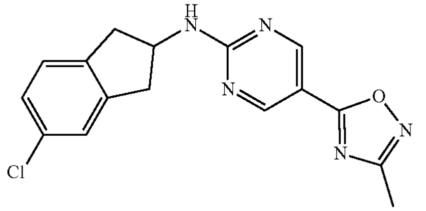 [SMILES: Cc1noc(-c2cnc(NC3Cc4ccc(Cl)cc4C3)nc2)n1]

To a suspension of 2-((5-chloro-2,3-dihydro-1H-inden-2-yl)amino)pyrimidine-5-carboxylic acid (60 mg, 207 μmol, intermediate B1) in N,N-dimethylformamide dry (800 μl) under nitrogen at room temperature, was added 1,1'-carbonyldiimidazole (38.1 mg, 228 μmol). The reaction mixture was stirred at room temperature for 30 minutes. Then (E)-N'-hydroxyacetimidamide (17.8 mg, 228 μmol) was added. The reaction mixture was heated to 115° C. for 19 hours. The reaction mixture was cooled to room temperature and the solvent was removed in vacuo. The crude solid was purified with flash column chromatography over silica gel using a gradient ethylacetate/heptane 0-40% to provide the title compound as a white solid (26 mg, 38% yield). MS (ESI): m/z=328.2 $[M+H]^+$ Example 2: N-(5-chloro-2,3-dihydro-1H-inden-2-yl)-5-(5-methyl-1,3,4-oxadiazol-2-yl)pyrimidin-2-amine

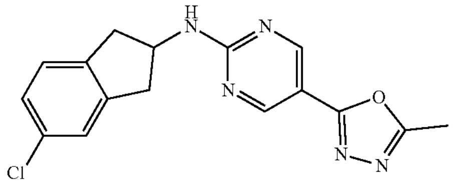 [SMILES: Cc1nnc(-c2cnc(NC3Cc4ccc(Cl)cc4C3)nc2)o1]

Step 1: N'-acetyl-2-((5-chloro-2,3-dihydro-1H-inden-2-yl)amino)pyrimidine-5-carbohydrazide

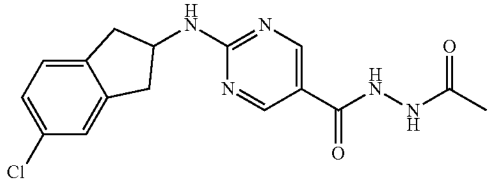 [SMILES: CC(=O)NNC(=O)c1cnc(NC2Cc3ccc(Cl)cc3C2)nc1]

In a sealed tube, to a solution of 2-((5-chloro-2,3-dihydro-1H-inden-2-yl)amino)pyrimidine-5-carboxylic acid (100 mg, 345 μmol, intermediate B1) in dichloromethane (3.8 ml) under nitrogen at room temperature, were added HOBt (74.9 mg, 554 μmol, Eq: 1.61), EDCI HCl (108 mg, 554 μmol), triethylamine (87.3 mg, 120 μl, 863 μmol, Eq: 2.5) and finally N,N-dimethylformamide (633 μl). Argon was bubbled through the mixture during 10 minutes. After that, acetohydrazide (25.6 mg, 345 μmol, Eq: 1) was added. The reaction mixture was stirred at room temperature for 3 hours. The mixture was quenched with water. The resulting solid was filtered, rinsed with water and dried to provide the title compound (80 mg, 67% yield) as a light brown solid. MS (ESI): m/z=346.2 $[M+H]^+$ Step 2: N-(5-chloro-2,3-dihydro-1H-inden-2-yl)-5-(5-methyl-1,3,4-oxadiazol-2-yl)pyrimidin-2-amine

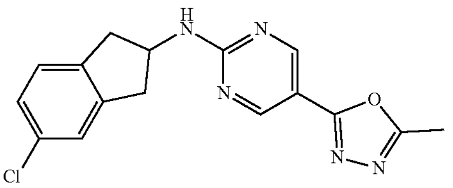 [SMILES: Cc1nnc(-c2cnc(NC3Cc4ccc(Cl)cc4C3)nc2)o1]

To a suspension of N'-acetyl-2-((5-chloro-2,3-dihydro-1H-inden-2-yl)amino)pyrimidine-5-carbohydrazide (78 mg, 226 μmol) in acetonitrile (2 ml) under nitrogen at room temperature, were added triethylamine (68.5 mg, 94.2 μl, 677 μmol) and 4-methylbenzenesulfonyl chloride (65.2 mg, 338 μmol). The reaction mixture was stirred at room temperature over week-end. The mixture was quenched with sat. sodium bicarbonate solution. The resulting precipitate was filtered, rinsed with water and dried. The crude compound (77 mg) was purified with flash column chromatography over silica gel using a gradient ethylacetate/heptane 0-80% to provide the title compound as an off-white solid (45 mg, 61% yield). MS (ESI): m/z=328.2 $[M+H]^+$ Example 3: N-(5-chloro-2,3-dihydro-1H-inden-2-yl)-5-(4-methyloxazol-2-yl)pyrimidin-2-amine

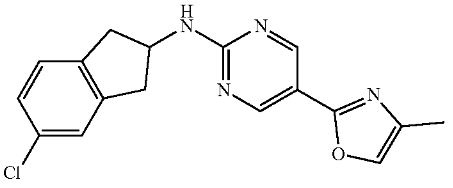 [SMILES: Cc1coc(-c2cnc(NC3Cc4ccc(Cl)cc4C3)nc2)n1]

Step 1: 2-((5-chloro-2,3-dihydro-1H-inden-2-yl)amino)-N-(1-hydroxypropan-2-yl)pyrimidine-5-carboxamide

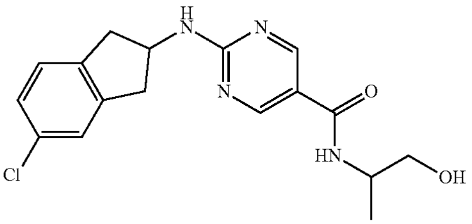 [SMILES: CC(CO)NC(=O)c1cnc(NC2Cc3ccc(Cl)cc3C2)nc1]

To a solution of 2-((5-chloro-2,3-dihydro-1H-inden-2-yl)amino)pyrimidine-5-carboxylic acid (200 mg, 690 μmol, intermediate B1) in N,N-dimethylformamide (4 ml) under nitrogen at room temperature, were added 2-aminopropan-1-ol (104 mg, 107 μl, 1.38 mmol), EDCI HCl (162 mg, 828 μmol, Eq: 1.2) and HOBt (112 mg, 828 μmol, Eq: 1.2). The reaction mixture was stirred at room temperature for 18 hours. The mixture was quenched with sat. aq. Soium bicarbonate solution. Water was added. The resulting suspension was stirred at room temperature for 10 minutes and filtered. The brown solid was suspended in diethyl ether, filtered and dried to provide the title compound (127 mg, 53% yield) as a light brown solid. MS (ESI): m/z=347.3 $[M+H]^+$ Step 2: 2-((5-chloro-2,3-dihydro-1H-inden-2-yl)amino)-N-(1-oxopropan-2-yl)pyrimidine-5-carboxamide

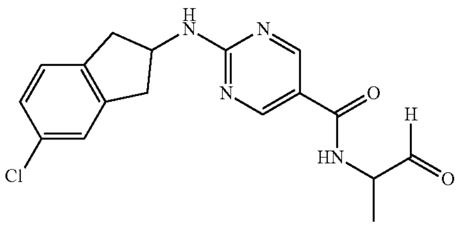 [SMILES: CC(C=O)NC(=O)c1cnc(NC2Cc3ccc(Cl)cc3C2)nc1]

To a solution of 2-((5-chloro-2,3-dihydro-1H-inden-2-yl)amino)-N-(1-hydroxypropan-2-yl)pyrimidine-5-carboxamide (126 mg, 363 μmol) in dichloromethane (4.5 ml) under nitrogen at 0° C., was added Dess-Martin periodinane (235 mg, 537 μmol). The reaction mixture was stirred at room temperature for 2.5 hours. The mixture was quenched with sat. aq. bicarbonate solution. Water and dichloromethane were added. Both layers were separated. The aqueous one was extracted twice with dichloromethane. The combined organic layers were dried over sodium sulfate and evaporated. The crude compound was purified with flash column chromatography over silica gel using a gradient ethylacetate/heptane 0-90% to provide the title compound as a light brown solid (104 mg, 83% yield). MS (ESI): m/z=345.3 $[M+H]^+$ Step 3: N-(5-chloro-2,3-dihydro-1H-inden-2-yl)-5-(4-methyloxazol-2-yl)pyrimidin-2-amine

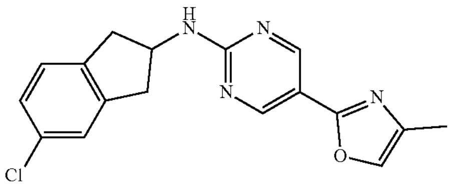 [SMILES: Cc1coc(-c2cnc(NC3Cc4ccc(Cl)cc4C3)nc2)n1]

A solution of 2-((5-chloro-2,3-dihydro-1H-inden-2-yl)amino)-N-(1-oxopropan-2-yl)pyrimidine-5-carboxamide (67 mg, 194 μmol) in Eaton's reagent (Phosphorus pentoxide, 7.7 wt. % in methanesulfonic acid) (1.94 g, 1.3 ml, 8.17 mmol) was stirred under microwave irradiation at 80° C. for 10 minutes, then at 100° C. for 10 minutes. The mixture was cooled to 0° C. and 5N NaOH was carefully added. The mixture was stirred at room temperature for 2 hours. Then ethyl acetate was added and both layers were separated. The aqueous layer was extracted twice with ethyl acetate, the combined organic layers were dried over sodium sulfate and evaporated. The crude brown semi-solid (100 mg) was purified with flash column chromatography over silica gel using a gradient ethylacetate/heptane 0-60% to provide the title compound as an off-white solid (6 mg, 10% yield). MS (ESI): m/z=327.2 [M+H]$^+$ Example 4: N-(5-chloro-2,3-dihydro-1H-inden-2-yl)-5-(3-methylisoxazol-5-yl)pyrimidin-2-amine

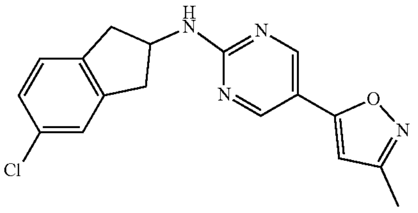 [SMILES: Cc1cc(-c2cnc(NC3Cc4ccc(Cl)cc4C3)nc2)on1]

The title compound was prepared in analogy to intermediate B6 from 5-bromo-N-(5-chloro-2,3-dihydro-1H-inden-2-yl)pyrimidin-2-amine (intermediate B2) and 3-methyl-5-(4,4,5,5-tetramethyl-1,3,2-dioxaborolan-2-yl)isoxazole as a white solid. MS (ESI): m/z=327.2 [M+H]$^+$ Example 5: N-(5-chloro-2,3-dihydro-1H-inden-2-yl)-5-(oxazol-2-yl)pyrimidin-2-amine

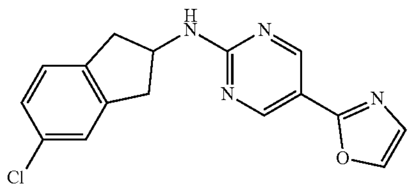 [SMILES: Clc1ccc2c(c1)CC(Nc1ncc(-c3ncco3)cn1)C2]

The title compound was prepared in analogy to intermediate B7 from 5-bromo-N-(5-chloro-2,3-dihydro-1H-inden-2-yl)pyrimidin-2-amine (intermediate B2) and 2-(tributylstannyl)oxazole as a white solid. MS (ESI): m/z=313.2 [M+H]$^+$ Example 6: N-(5-chloro-2,3-dihydro-1H-inden-2-yl)-5-(pyrazin-2-yl)pyrimidin-2-amine

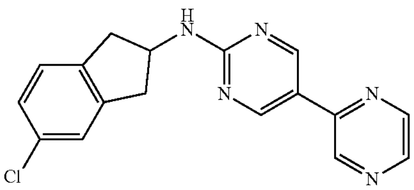 [SMILES: Clc1ccc2c(c1)CC(Nc1ncc(-c3cnccn3)cn1)C2]

The title compound was prepared in analogy to intermediate B7 from 5-bromo-N-(5-chloro-2,3-dihydro-1H-inden-2-yl)pyrimidin-2-amine (intermediate B2) and 2-(tributylstannyl)pyrazine as an off-white solid. MS (ESI): m/z=324.2 [M+H]$^+$ Example 7: N-(5-chloro-2,3-dihydro-1H-inden-2-yl)-5-(4-methyl-1H-pyrazol-1-yl)pyrimidin-2-amine

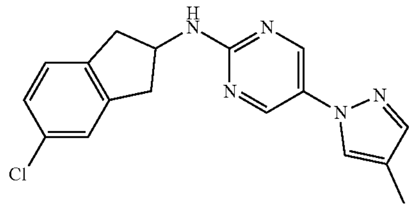 [SMILES: Cc1cnn(-c2cnc(NC3Cc4ccc(Cl)cc4C3)nc2)c1]

The title compound was prepared in analogy to intermediate B11 from 5-bromo-N-(5-chloro-2,3-dihydro-1H-inden-2-yl)pyrimidin-2-amine (intermediate B2) and 4-methyl-1H-pyrazole as a white solid. MS (ESI): m/z=326.2 [M+H]$^+$ Example 8: N-(5-chloro-2,3-dihydro-1H-inden-2-yl)-5-(3-methyl-1H-pyrazol-1-yl)pyrimidin-2-amine

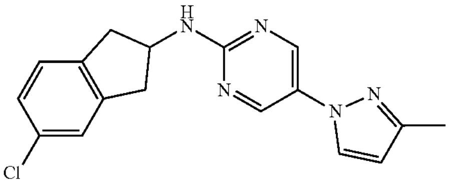 [SMILES: Cc1ccn(-c2cnc(NC3Cc4ccc(Cl)cc4C3)nc2)n1]

The title compound was prepared in analogy to intermediate B11 from 5-bromo-N-(5-chloro-2,3-dihydro-1H-inden-2-yl)pyrimidin-2-amine (intermediate B2) and 3-methyl-1H-pyrazole as a white solid. MS (ESI): m/z=326.2 [M+H]$^+$ Example 9: N-(5-chloro-2,3-dihydro-1H-inden-2-yl)-5-(4-methyltriazol-2-yl)pyrimidin-2-amine

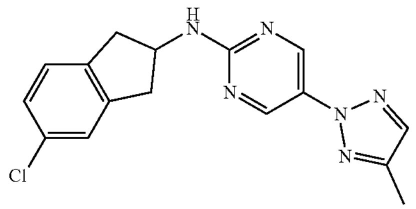 [SMILES: Cc1cnn(-c2cnc(NC3Cc4ccc(Cl)cc4C3)nc2)n1]

The title compound was prepared in analogy to intermediate B11 from 5-bromo-N-(5-chloro-2,3-dihydro-1H-inden-2-yl)pyrimidin-2-amine (intermediate B2) and 4-methyl-1H-1,2,3-triazole as an off-white solid. MS (ESI): m/z=327.2 [M+H]$^+$ Example 10: N-(5-chloro-2,3-dihydro-1H-inden-2-yl)-5-(5-methyloxazol-2-yl)pyrimidin-2-amine

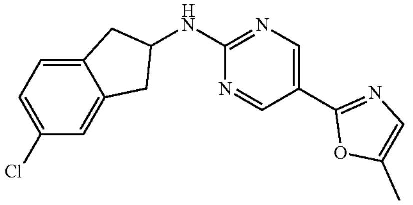 [SMILES: Cc1cnc(-c2cnc(NC3Cc4ccc(Cl)cc4C3)nc2)o1]

The title compound was prepared in analogy to intermediate B8 from N-(5-chloro-2,3-dihydro-1H-inden-2-yl)-5-(4,4,5,5-tetramethyl-1,3,2-dioxaborolan-2-yl)pyrimidin-2-amine (intermediate B3) and 2-bromo-5-methyloxazole as a white solid. MS (ESI): m/z=327.2 $[M+H]^+$ Example 11: N-(5-chloro-2,3-dihydro-1H-inden-2-yl)-5-(pyridazin-3-yl)pyrimidin-2-amine

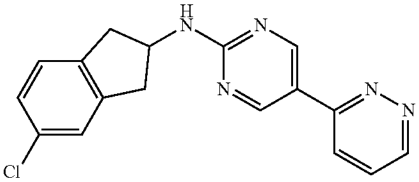 [SMILES: Clc1ccc2c(c1)CC(Nc1ncc(-c3cccnn3)cn1)C2]

The title compound was prepared in analogy to intermediate B8 from N-(5-chloro-2,3-dihydro-1H-inden-2-yl)-5-(4,4,5,5-tetramethyl-1,3,2-dioxaborolan-2-yl)pyrimidin-2-amine (intermediate B3) and 3-chloropyridazine hydrochloride as a light yellow solid. MS (ESI): m/z=324.2 $[M+H]^+$ Example 12: (S or R)—N-(5-chloro-2,3-dihydro-1H-inden-2-yl)-5-(3-methyl-1,2,4-oxadiazol-5-yl)pyrimidin-2-amine

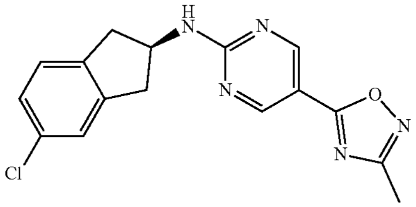 [SMILES: Cc1noc(-c2cnc(N[C@@H]3Cc4ccc(Cl)cc4C3)nc2)n1]

and

Example 13: (R or S)—N-(5-chloro-2,3-dihydro-1H-inden-2-yl)-5-(3-methyl-1,2,4-oxadiazol-5-yl)pyrimidin-2-amine

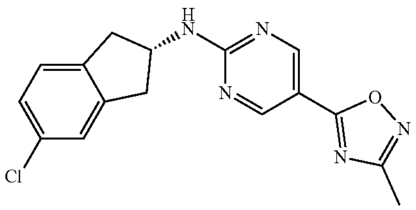 [SMILES: Cc1noc(-c2cnc(N[C@H]3Cc4ccc(Cl)cc4C3)nc2)n1]

Chiral separation of racemic mixture: N-(5-chloro-2,3-dihydro-1H-inden-2-yl)-5-(3-methyl-1,2,4-oxadiazol-5-yl)pyrimidin-2-amine (example 1) using OD-H, 12 n, 5 μm, 250×4.6 mm as chiral column, under SFC conditions provided Example 12: (S or R)—N-(5-chloro-2,3-dihydro-1H-inden-2-yl)-5-(3-methyl-1,2,4-oxadiazol-5-yl)pyrimidin-2-amine as the first eluting enantiomer (off-white solid, retention time: 3.89 min, 100% ee, MS (ESI): m/z=328.2 $[M+H]^+$) and Example 13: (R or S)—N-(5-chloro-2,3-dihydro-1H-inden-2-yl)-5-(3-methyl-1,2,4-oxadiazol-5-yl)pyrimidin-2-amine as the second eluting enantiomer (off-white solid, retention time: 4.22 min, 80% ee, MS (ESI): m/z=328.2 $[M+H]^+$ Example 14: N-(5-chloro-2,3-dihydro-1H-inden-2-yl)-5-(5,5-dimethyl-4,5-dihydroisoxazol-3-yl)pyrimidin-2-amine

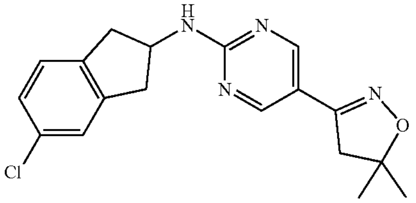 [SMILES: CC1(C)CC(c2cnc(NC3Cc4ccc(Cl)cc4C3)nc2)=NO1]

The title compound was prepared in analogy to intermediate B2 from 3-(2-chloropyrimidin-5-yl)-5,5-dimethyl-4,5-dihydroisoxazole (intermediate B4) and 5-chloro-2,3-dihydro-1H-inden-2-amine hydrochloride (intermediate A1) as an off-white solid. MS (ESI): m/z=343.3 $[M+H]^+$ Example 15: (S)-6-chloro-2-((5-(3-methyl-1,2,4-oxadiazol-5-yl)pyrimidin-2-yl)amino)-2,3-dihydro-1H-indene-4-carbonitrile

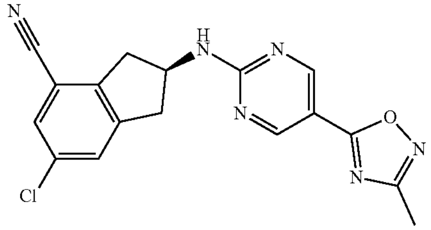 [SMILES: Cc1noc(-c2cnc(N[C@H]3Cc4cc(Cl)cc(C#N)c4C3)nc2)n1]

Step 1: 3-methyl-5-(2-(methylsulfonyl)pyrimidin-5-yl)-1,2,4-oxadiazole

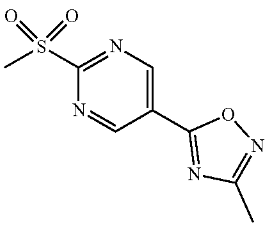 [SMILES: Cc1noc(-c2cnc(S(C)(=O)=O)nc2)n1]

To a colorless solution of 3-methyl-5-(2-(methylthio)pyrimidin-5-yl)-1,2,4-oxadiazole—(50 mg, 240 μmol, intermediate B5) in dichloromethane (2 ml) under nitrogen at 0° C., was added 3-chloroperoxybenzoic acid (113 mg, 504 μmol). The reaction mixture was allowed to warm to room temperature and stirred over weekend. The resulting white suspension was diluted with dichloromethane. A saturated sodium bicarbonate solution was added. Both layers were separated and the aqueous one was extracted twice with dichloromethane. The combined organic layers were dried over sodium sulfate and concentrated in vacuo. The crude off-white solid (50 mg) was purified with flash column chromatography over silica gel using a gradient ethylacetate/heptane 0-50% to provide the title compound as a white solid (29 mg, 50% yield). MS (ESI): m/z=241.1 [M+H]$^+$ Step 2: (S)-6-chloro-2-((5-(3-methyl-1,2,4-oxadiazol-5-yl)pyrimidin-2-yl)amino)-2,3-dihydro-1H-indene-4-carbonitrile

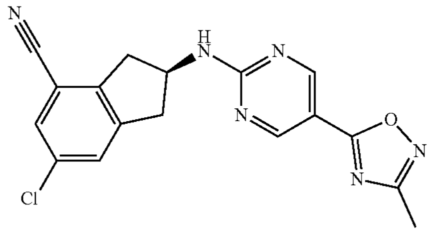 [SMILES: Cc1noc(-c2cnc(N[C@H]3Cc4cc(Cl)cc(C#N)c4C3)nc2)n1]

To a stirred suspension of 3-methyl-5-(2-(methylsulfonyl)pyrimidin-5-yl)-1,2,4-oxadiazole (28.5 mg, 119 μmol) in N,N-dimethylacetamide (2.3 ml) under nitrogen at room temperature, were added (S)-2-amino-6-chloro-2,3-dihydro-1H-indene-4-carbonitrile hydrochloride (26 mg, 108 μmol, intermediate A2) and N,N-diisopropylethylamine (28.4 mg, 37.6 μl, 216 μmol). The reaction mixture was stirred at room temperature for 1 hour. The resulting orange solution was poured into water and extracted three times with ethyl acetate. The combined organic layers were dried over sodium sulfate and concentrated in vacuo. The crude light yellow semi-solid was purified with flash column chromatography over silica gel using a gradient ethylacetate/heptane 0-50% to provide the title compound as a white solid (18 mg, 47% yield). MS (ESI): m/z=353.2 [M+H]$^+$ The following examples 16-21 were prepared in analogy to example 15 in 2 steps from intermediate A2 and the indicated thiomethyl intermediates B6-11.

| Ex. | Structure | Name | Int. B | MS (ESI): m/z, [M + H]$^+$ |
|---|---|---|---|---|
| 16 | 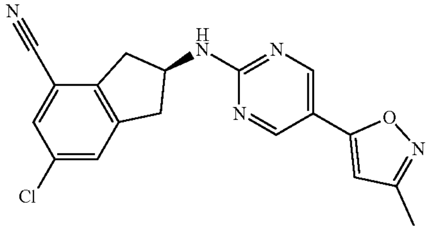 | (S)-6-chloro-2-((5-(3-methylisoxazol-5-yl)pyrimidin-2-yl)amino)-2,3-dihydro-1H-indene-4-carbonitrile | B6 | 352.2 |
| 17 | 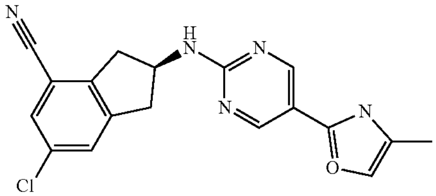 | (S)-6-chloro-2-((5-(4-methyloxazol-2-yl)pyrimidin-2-yl)amino)-2,3-dihydro-1H-indene-4-carbonitrile | B7 | 352.2 |
| 18 | 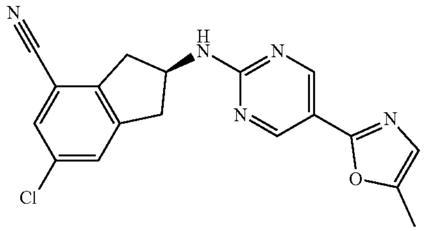 [SMILES: Cc1cnc(-c2cnc(N[C@H]3Cc4cc(Cl)cc(C#N)c4C3)nc2)o1] | (S)-6-chloro-2-((5-(5-methyloxazol-2-yl)pyrimidin-2-yl)amino)-2,3-dihydro-1H-indene-4-carbonitrile | B8 | 352.1 |
| 19 | 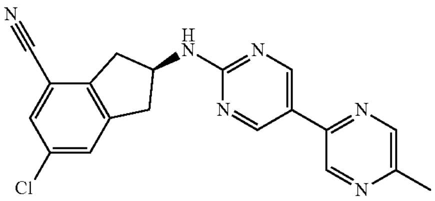 [SMILES: Cc1cnc(-c2cnc(N[C@H]3Cc4cc(Cl)cc(C#N)c4C3)nc2)cn1] | (S)-6-chloro-2-((5-(5-methylpyrazin-2-yl)pyrimidin-2-yl)amino)-2,3-dihydro-1H-indene-4-carbonitrile | B9 | 363.2 |

-continued

| Ex. | Structure | Name | Int. B | MS (ESI): m/z, $[M + H]^+$ |
|---|---|---|---|---|
| 20 | 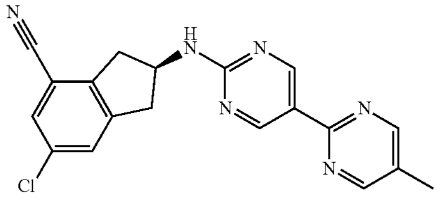 [SMILES: Cc1cnc(-c2cnc(N[C@H]3Cc4cc(Cl)cc(C#N)c4C3)nc2)nc1] | (S)-6-chloro-2-((5-methyl-[2,5"-bipyrimidin]-2"-yl)amino)2,3-dihydro-1H-indene-4-carbonitrile' | B10 | 363.2 |
| 21 | 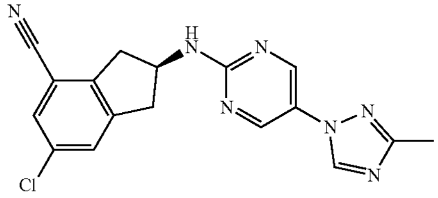 [SMILES: Cc1ncn(-c2cnc(N[C@H]3Cc4cc(Cl)cc(C#N)c4C3)nc2)n1] | (S)-6-chloro-2-[[5-(3-methyl-1,2,4-triazol-1-yl)pyrimidin-2-yl]amino]-2,3-dihydro-1H-indene-4-carbonitrile | B11 | 352.2 |

Example A

A compound of formula I can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropyl | 20 mg |
| methylcellulose | 425 mg |

Example B

A compound of formula I can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula I

I

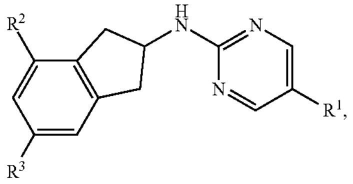

or a pharmaceutically acceptable salt thereof, wherein:

$R^1$ is selected from the group consisting of
i) 5- or 6-member heteroaryl,
ii) substituted 5- or 6-member heteroaryl,
iii) 5- or 6-member heterocycloalkyl, and
iv) substituted 5- or 6-member heterocycloalkyl, wherein the substituted 5- or 6-member heteroaryl or substituted 5- or 6-member heterocycloalkyl is substituted with one or more $C_{1-6}$-alkyl substituents;

$R^2$ is selected from the group consisting of
i) H,
ii) cyano,
iii) halogen,
iv) $C_{1-6}$-alkyl, and
v) halo-$C_{1-6}$-alkyl; and $R^3$ is halogen.

2. A compound according to claim 1, or a pharmaceutically acceptable salt thereof, wherein $R^3$ is Cl.

3. A compound according to claim 1, or a pharmaceutically acceptable salt thereof, wherein $R^2$ is selected from the group consisting of:
i) H, and
ii) cyano.

4. A compound according to claim 1, or a pharmaceutically acceptable salt thereof, wherein:

$R^1$ is selected from the group consisting of
i) 5- or 6-member heteroaryl,
ii) substituted 5- or 6-member heteroaryl, and
iii) substituted 5- or 6-member heterocycloalkyl, wherein the substituted 5- or 6-member heteroaryl or substituted 5- or 6-member heterocycloalkyl is substituted with one or more $C_{1-6}$-alkyl substituents; and $R^2$ is selected from the group consisting of
i) H, and
ii) cyano.

5. A compound according to claim 1, or a pharmaceutically acceptable salt thereof, wherein;

$R^1$ is selected from the group consisting of
i) 5- or 6-member heteroaryl,
ii) substituted 5- or 6-member heteroaryl, and
iii) substituted 5- or 6-member heterocycloalkyl, wherein the substituted 5- or 6-member heteroaryl or substituted 5- or 6-member heterocycloalkyl is substituted with one or more $C_{1-6}$-alkyl substituents;

$R^2$ is selected from the group consisting of
i) H, and
ii) cyano; and
$R^3$ is Cl.

6. A compound according to claim 1, or a pharmaceutically acceptable salt thereof, wherein $R^1$ is selected from the group consisting of 3-methyl-1,2,4-oxadiazol-5-yl, 3-methyl-1,2,4-triazol-1-yl, 3-methylisoxazol-5-yl, 3-methylpyrazol-1-yl, 4-methyloxazol-2-yl, 4-methylpyrazol-1-yl, 4-methyltriazol-2-yl, 5,5-dimethyl-4H-isoxazol-3-yl, 5-methyl-1,3,4-oxadiazol-2-yl, 5-methyloxazol-2-yl, 5-methylpyrazin-2-yl, 5-methylpyrimidin-2-yl, oxazol-2-yl, pyrazin-2-yl, and pyridazin-3-yl.

7. A compound according to claim 1, or a pharmaceutically acceptable salt thereof, wherein:
$R^1$ is selected from the group consisting of 3-methyl-1,2,4-oxadiazol-5-yl, 3-methyl-1,2,4-triazol-1-yl, 3-methylisoxazol-5-yl, 3-methylpyrazol-1-yl, 4-methyloxazol-2-yl, 4-methylpyrazol-1-yl, 4-methyltriazol-2-yl, 5,5-dimethyl-4H-isoxazol-3-yl, 5-methyl-1,3,4-oxadiazol-2-yl, 5-methyloxazol-2-yl, 5-methylpyrazin-2-yl, 5-methylpyrimidin-2-yl, oxazol-2-yl, pyrazin-2-yl, and pyridazin-3-yl;
$R^2$ is selected from the group consisting of
i) H, and
ii) cyano; and
$R^3$ is Cl.

8. A compound according to claim 1, selected from the group consisting of
N-(5-chloro-2,3-dihydro-1H-inden-2-yl)-5-(3-methyl-1,2,4-oxadiazol-5-yl)pyrimidin-2-amine;
N-(5-chloro-2,3-dihydro-1H-inden-2-yl)-5-(5-methyl-1,3,4-oxadiazol-2-yl)pyrimidin-2-amine;
N-(5-chloro-2,3-dihydro-1H-inden-2-yl)-5-(4-methyloxazol-2-yl)pyrimidin-2-amine;
N-(5-chloro-2,3-dihydro-1H-inden-2-yl)-5-(3-methylisoxazol-5-yl)pyrimidin-2-amine;
N-(5-chloro-2,3-dihydro-1H-inden-2-yl)-5-(4-methyl-1H-pyrazol-1-yl)pyrimidin-2-amine;
N-(5-chloro-2,3-dihydro-1H-inden-2-yl)-5-(3-methyl-1H-pyrazol-1-yl)pyrimidin-2-amine;
N-(5-chloro-2,3-dihydro-1H-inden-2-yl)-5-(4-methyltriazol-2-yl)pyrimidin-2-amine;
N-(5-chloro-2,3-dihydro-1H-inden-2-yl)-5-(5-methyloxazol-2-yl)pyrimidin-2-amine;
(S or R)—N-(5-chloro-2,3-dihydro-1H-inden-2-yl)-5-(3-methyl-1,2,4-oxadiazol-5-yl)pyrimidin-2-amine;
(R or S)—N-(5-chloro-2,3-dihydro-1H-inden-2-yl)-5-(3-methyl-1,2,4-oxadiazol-5-yl)pyrimidin-2-amine;
N-(5-chloro-2,3-dihydro-1H-inden-2-yl)-5-(5,5-dimethyl-4,5-dihydroisoxazol-3-yl)pyrimidin-2-amine;
(S)-6-chloro-2-((5-(3-methyl-1,2,4-oxadiazol-5-yl)pyrimidin-2-yl)amino)-2,3-dihydro-1H-indene-4-carbonitrile;
(S)-6-chloro-2((5-(3-methylisoxazol-5-yl)pyrimidin-2-yl)amino)-2,3-dihydro-1H-indene-4-carbonitrile;
(S)-6-chloro-2-((5-(4-methyloxazol-2-yl)pyrimidin-2-yl)amino)-2,3-dihydro-1H-indene-4-carbonitrile;
(S)-6-chloro-2-((5-(5-methyloxazol-2-yl)pyrimidin-2-yl)amino)-2,3-dihydro-1H-indene-4-carbonitrile;
(S)-6-chloro-2-((5-(5-methylpyrazin-2-yl)pyrimidin-2-yl)amino)-2,3-dihydro-1H-indene-4-carbonitrile;
(S)-6-chloro-2-((5-methyl-[2,5"-bipyrimidin]-2"-yl)amino)-2,3-dihydro-1H-indene-4-carbonitrile; and
(S)-6-chloro-2-[[5-(3-methyl-1,2,4-triazol-1-yl)pyrimidin-2-yl]amino]-2,3-dihydro-1H-indene-4-carbonitrile;
or a pharmaceutically acceptable salt thereof.

9. A process to prepare a compound according to claim 1, or a pharmaceutically acceptable salt thereof, the process comprising the reaction of a compound of formula II with a compound of formula III to provide a compound of formula I, wherein $R^1$, $R^2$, and $R^3$ are as defined in claim 1 and X is halogen or a thiomethyl group:

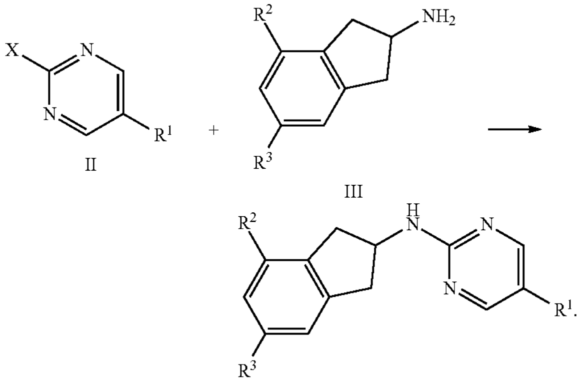

II

III

I

10. A pharmaceutical composition comprising a compound according to claim 1, or a pharmaceutically acceptable salt thereof, and a therapeutically inert carrier.

11. A pharmaceutical composition comprising a compound according to claim 8, or a pharmaceutically acceptable salt thereof, and a therapeutically inert carrier.

* * * * *